(12) United States Patent
McAuliffe et al.

(10) Patent No.: US 7,212,868 B2
(45) Date of Patent: May 1, 2007

(54) ELECTRODE AND INSULATION ASSEMBLY FOR A LEAD AND METHOD THEREFOR (75) Inventors: Mark McAuliffe, Mounds View, MN (US); Jaime L. Rugnetta, White Bear Lake, MN (US); Brian D. Soltis, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 136 days.

(21) Appl. No.: 10/813,496

(22) Filed: Mar. 30, 2004

(65) Prior Publication Data
US 2005/0222660 A1 Oct. 6, 2005

(51) Int. Cl.
*A61N 1/05* (2006.01)
(52) U.S. Cl. .................. 607/116; 607/119; 600/373; 600/374
(58) Field of Classification Search ........ 600/372–374, 600/377; 607/122, 123
See application file for complete search history.

(56) References Cited

U.S. PATENT DOCUMENTS

| 4,590,950 | A | * | 5/1986 | Iwaszkiewicz et al. ..... 607/119 |
| 5,014,720 | A | | 5/1991 | Barcel et al. |
| 6,018,684 | A | | 1/2000 | Bartig et al. |
| 6,134,478 | A | | 10/2000 | Spehr |
| 6,456,888 | B1 | | 9/2002 | Skinner et al. |
| 6,526,321 | B1 | | 2/2003 | Spehr |
| 6,952,616 | B2 | * | 10/2005 | Wessman et al. ........... 607/122 |

* cited by examiner

*Primary Examiner*—Mark Bockelman
(74) *Attorney, Agent, or Firm*—Schwegman, Lundberg, Woessner & Kluth, P.A.

(57) ABSTRACT

A lead assembly includes an inner electrode coupled with a conductor, and an outer electrode disposed over the inner electrode, where the outer electrode is coupled with at least a portion of the inner electrode. Insulative material is disposed between a portion of the inner and outer electrodes, for example within a void between the inner and outer electrodes.

36 Claims, 5 Drawing Sheets

ELECTRODE AND INSULATION ASSEMBLY FOR A LEAD AND METHOD THEREFOR

TECHNICAL FIELD

Leads for conducting electrical signals to and from the heart, and more particularly, leads having an interconnect for one or more electrodes and the conductor.

TECHNICAL BACKGROUND

Pacemaker leads represent the electrical link between the pulse generator and the heart tissue, which is to be excited and/or sensed. These pacemaker leads include single or multiconductors that are connected to an electrode in an electrode assembly at an intermediate portion or distal end of a pacing lead. A connector is included at the proximal end to form the electrical connection with the pacemaker.

To implant the lead within the patient, the lead is often fed intravenously toward the heart, where the lead is implanted for long periods of time, i.e. chronically. During a chronic implant, the lead is subject to bodily fluids over a long period of time.

Accordingly, what is needed is a lead having a lead body with resistance to leakage. What is further needed is a lead that is manufacturable in a repeatable and reliable manner.

SUMMARY

A lead assembly includes an inner electrode coupled with a conductor, and an outer electrode disposed over the inner electrode, where the outer electrode is coupled with at least a portion of the inner electrode, for example with a coupling projection, such as an annular or a non-annular projection of the inner electrode. Optionally, means for aligning the outer electrode relative to the inner electrode are included. Insulative material is disposed between a portion of the inner and outer electrodes, for example within a void between the inner and outer electrodes. The insulative material, in one option, extends between the outer electrode inner surface to at least a portion of the inner electrode outer surface, and/or along the length of the inner electrode, thereby forming an internal bridge within the lead assembly.

Several options for the lead assembly are as follows. For example, in one option, the lead assembly includes alignment features for aligning the outer electrode with the inner electrode, such as alignment features on the outer electrode, i.e. a sight hole, or alignment features on the inner electrode, i.e. cross-hairs marked on the inner electrode.

Several variations for the coupling projection are also possible. For instance, in one option the coupling projection has a cross-section with one or more substantially flat sides. In another option, the coupling projection extends substantially from the first end to the second end, or has a length substantially as long as the inner electrode.

A method is further provided including coupling a conductor with an inner electrode, disposing insulative material over the conductor and inner electrode, disposing an outer electrode over the inner electrode and disposing the insulative material such that insulative material extends between an inner surface of the outer electrode and an outer surface of the inner electrode, or along a length of the inner electrode, for example with a preformed insulative component. The method further includes coupling the outer electrode with the inner electrode with an optional coupling projection of the inner electrode, for example by welding the outer electrode to the inner electrode. Another option, is coupling by laser welding.

Several options for the method are as follows. For instance, in one option the inner electrode includes a non-annular projection extending therefrom to which the outer electrode is coupled. In another option, the method further includes aligning the outer electrode with the inner electrode prior to coupling the outer electrode with the inner electrode. In yet another option, the method includes disposing one or more recesses over one or more coupling projections of the inner electrode.

These and other embodiments, aspects, advantages, and features will be set forth in part in the description which follows, and in part will become apparent to those skilled in the art by reference to the following description and referenced drawings or by practice thereof. The aspects, advantages, and features are realized and attained by means of the instrumentalities, procedures, and combinations particularly pointed out in the appended claims and their equivalents.

DESCRIPTION OF THE EMBODIMENTS

In the following detailed description, reference is made to the accompanying drawings, which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the spirit and scope of the present invention. Therefore, the following detailed description is not to be taken in a limiting sense, and the scope is defined by the appended claims.

Figure 1:
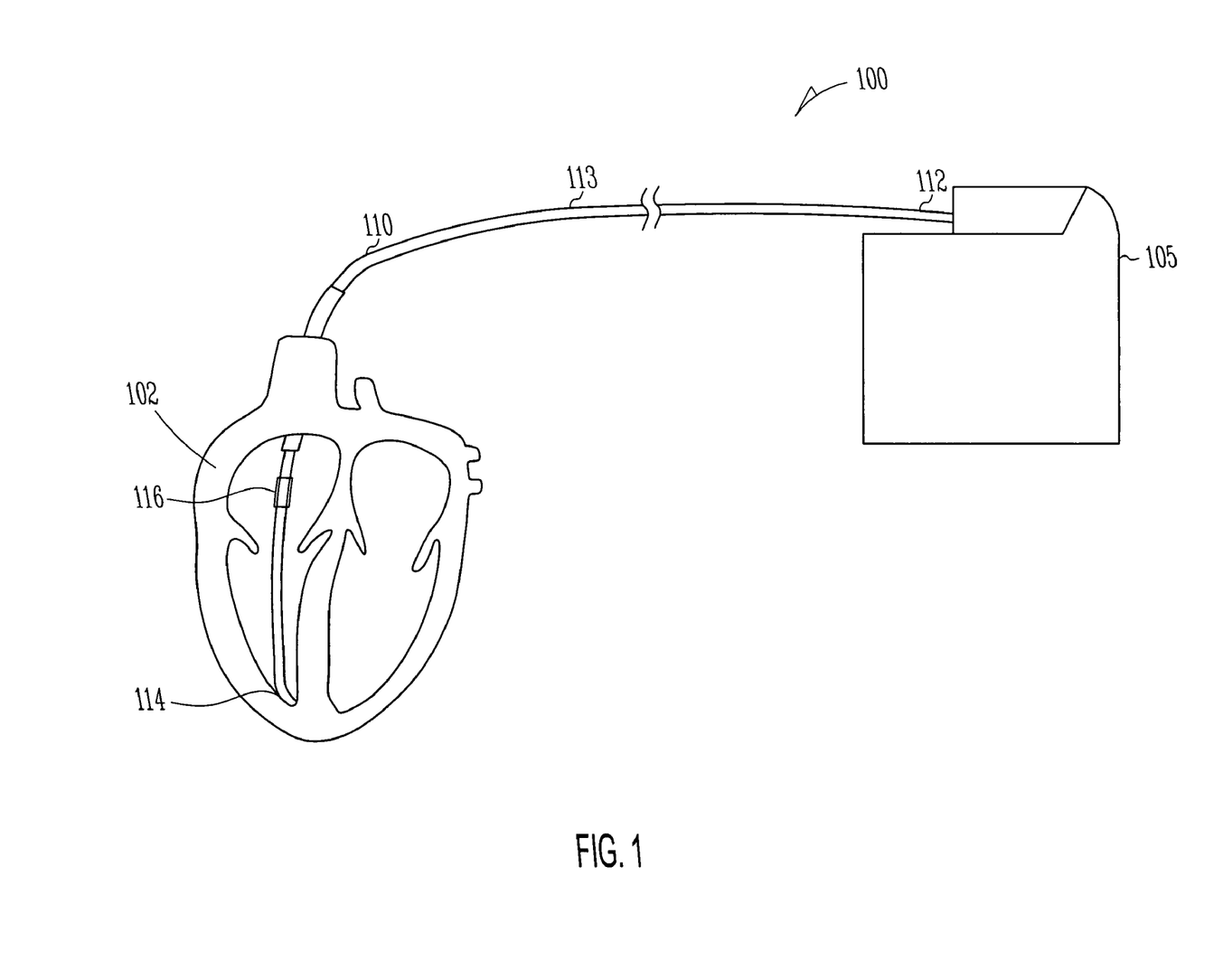
FIG. 1 is a diagram illustrating a lead system constructed in accordance with one embodiment.

A lead assembly 110 and lead system 100 are illustrated in FIG. 1. FIG. 1 is a diagram of a system 100 for delivering and/or receiving electrical pulses or signals to stimulate and/or sense the heart 102. The system 100 includes a pulse generator 105 and a lead 110. The pulse generator 105 includes a source of power as well as an electronic circuitry portion. The pulse generator 105, in one option, is a battery-powered device which generates a series of timed electrical discharges or pulses. The pulse generator 105 is generally implanted into a subcutaneous pocket made in the wall of the chest. Alternatively, the pulse generator 105 is placed in a subcutaneous pocket made in the abdomen, or in other locations.

The lead assembly 110 includes a lead body 113 which extends from a proximal end 112, where it is coupled with the pulse generator 105, as further discussed below. The lead assembly 110 extends to a distal end 114, which is coupled with a portion of a heart 102, when implanted. The distal end 114 of the lead assembly 110 includes at least one electrode assembly 116 which electrically couples the lead assembly 110 with the heart 102. At least one electrical conductor 120 (FIG. 2) is disposed within the lead assembly 110 and extends, in one option, from the proximal end 112 to the distal end 114 of the lead assembly 110. The at least one electrical conductor 120 electrically couples the electrode assembly 116 with the proximal end 112 of the lead assembly 110. The electrical conductors carry electrical current and pulses between the pulse generator 105 and the electrode assembly 116, and to and from the heart 102.

Figure 2:
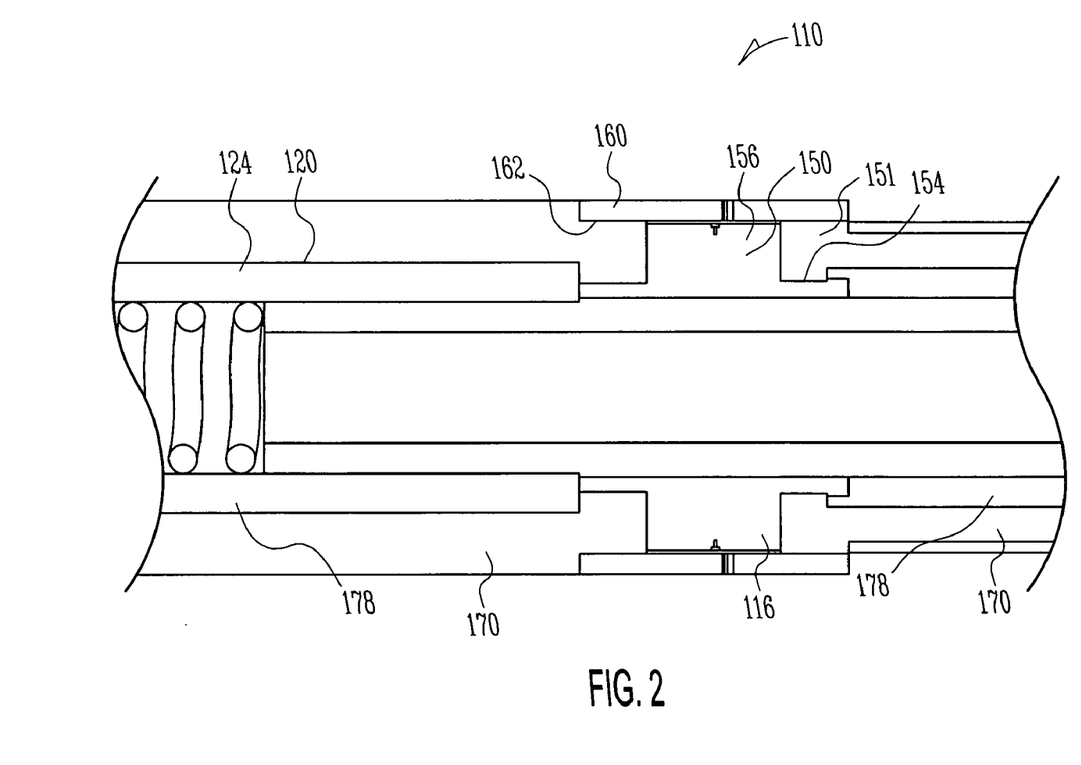
FIG. 2 is a cross-sectional view of a portion of a lead constructed in accordance with one embodiment.

Referring to FIG. 2, the lead assembly 110 includes at least one conductor 120, for example a coiled conductor or a cable conductor. In one option, a plurality of conductors is disposed therein. For example, a plurality of cable conductors is disposed within the lead body 110. In another option, a plurality of coiled conductors 124 is disposed within the lead body 110. The coiled conductors 124 include at least one filar, and optionally at least a portion of each individual filar is insulated. The at least one conductor extends from a proximal end to a distal end.

The lead assembly further includes the electrode assembly 116, that includes an inner electrode 150 and an outer electrode 160, where at least a portion of the inner electrode 150 is disposed within the outer electrode 160. A void 151 is defined between the inner electrode 150 and the outer electrode 160. For example, in one option, the void 151 is defined between an inner electrode outer surface 154, and an outer electrode inner surface 162. An insulative material 170 is disposed between a portion of the inner and outer electrodes 150, 160, for example, within the void 151. In one option, the insulative material 170 extends between the outer electrode inner surface 162 to at least a portion of the inner electrode outer surface 154. In another option, insulative material such as tubing 178, i.e. silicone tubing is disposed adjacent to the inner electrode 150.

Figure 4:
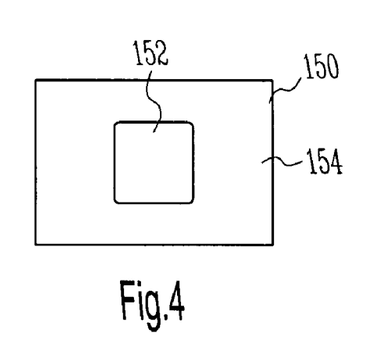
FIG. 4 is a top view of an inner electrode constructed in accordance with one embodiment.
Figure 5:
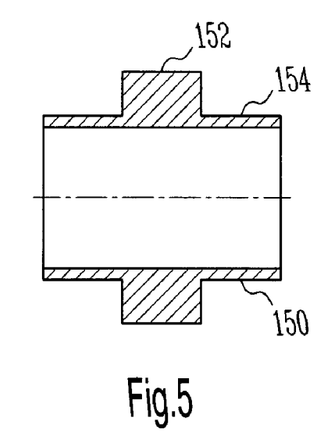
FIG. 5 is a cross-sectional view of an inner electrode constructed in accordance with one embodiment.
Figure 6:
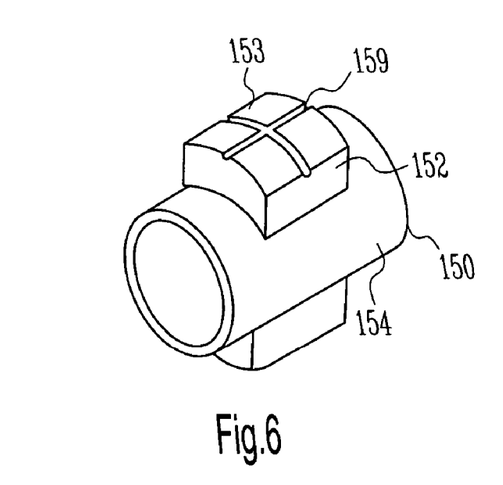
FIG. 6 is a perspective view of an inner electrode constructed in accordance with one embodiment.

FIGS. 4–8 illustrate the inner electrode 150 in greater detail. The inner electrode 150 and/or its various features discussed herein, in one option, is formed by processes including, but not limited to machining, injection molding of conductive material, or by EDM. In one option, for example as shown in FIG. 4, the inner electrode 150 includes one or more coupling projections 152, for example one or more coupling projections 152 with one or more flat sides, that extends from an outer surface 154 of the inner electrode 150. In one option, as illustrated in FIGS. 4–6, the one or more coupling projections 152 has a substantially square shaped cross-section. In another option, an outer surface 153 of the one or more coupling projections 152 has a surface to mate with the interior surface of the outer electrode. For example, the outer surface 153 includes a slightly rounded outer profile. Other profiles are suitable as well. In another option, the one or more coupling projections, for example along the outer surface 153, include alignment features 159. For instance, in one option, the alignment features 159 include cross-hairs formed or printed or etched on a portion of the inner electrode 150, and allow for the inner electrode, for example the coupling projection 152 of the inner electrode 150 to be aligned with the outer electrode.

Figure 7:
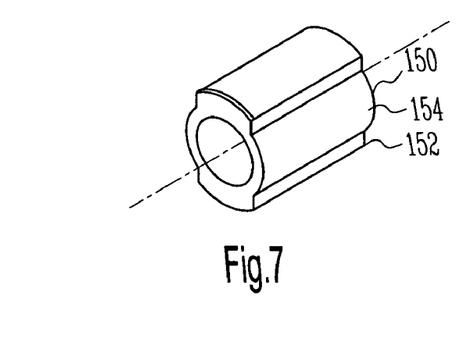
FIG. 7 is a perspective view of an inner electrode constructed in accordance with one embodiment.
Figure 8:
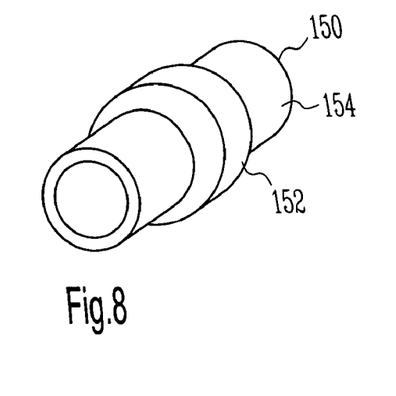
FIG. 8 is a perspective view of an inner electrode constructed in accordance with one embodiment.

FIGS. 7 and 8 illustrate additional options for the one or more coupling projections 152. For example, in one option, the one or more coupling projections 152 includes an annular shaped projection that extends around a perimeter of the inner electrode 150, as illustrated in FIG. 8. In another option, the one or more coupling projections 152 include two or more projections extending from the outer surface 154 of the inner electrode 150, and optionally for substantially the same length as the length of the inner electrode 150, as illustrated in FIG. 7. For each of the options, the one or more coupling projections 152 are designed to couple the inner electrode 150 with the outer electrode 160, for example as illustrated in FIG. 10.

In one option, the outer electrode 160 surrounds an outer perimeter of the inner electrode 150, and the one or more projections 152 are used to couple the components together. For example, in one option, the outer electrode 160 is welded to the inner electrode 150, for example, by laser welding. Other mechanical attachment methods can be used as well.

Figure 9:
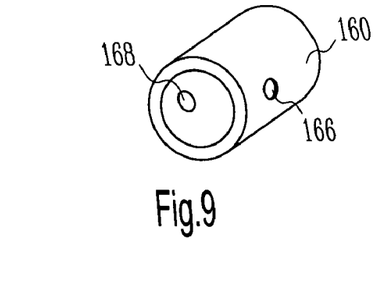
FIG. 9 is a perspective view of an outer electrode constructed in accordance with one embodiment.

The outer electrode 160, in one option, includes a ring electrode as illustrated in FIG. 9. The outer electrode 160, in one option, is formed by processes including, but not limited to machining, injection molding of conductive material, or by EDM. In one option, the outer electrode 160 includes one or more outer electrode alignment features 166 therein. In one option, the alignment features 166 include a sight hole 168 that can be used to align the outer electrode 160 with alignment features of the inner electrode, for example, cross-hairs of the inner electrode.

Figure 10:
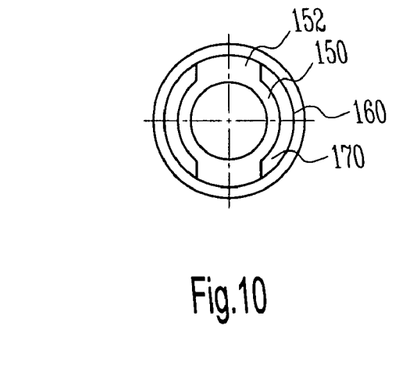
FIG. 10 is an end view of the outer and inner electrodes constructed in accordance with one embodiment.
Figure 11A:
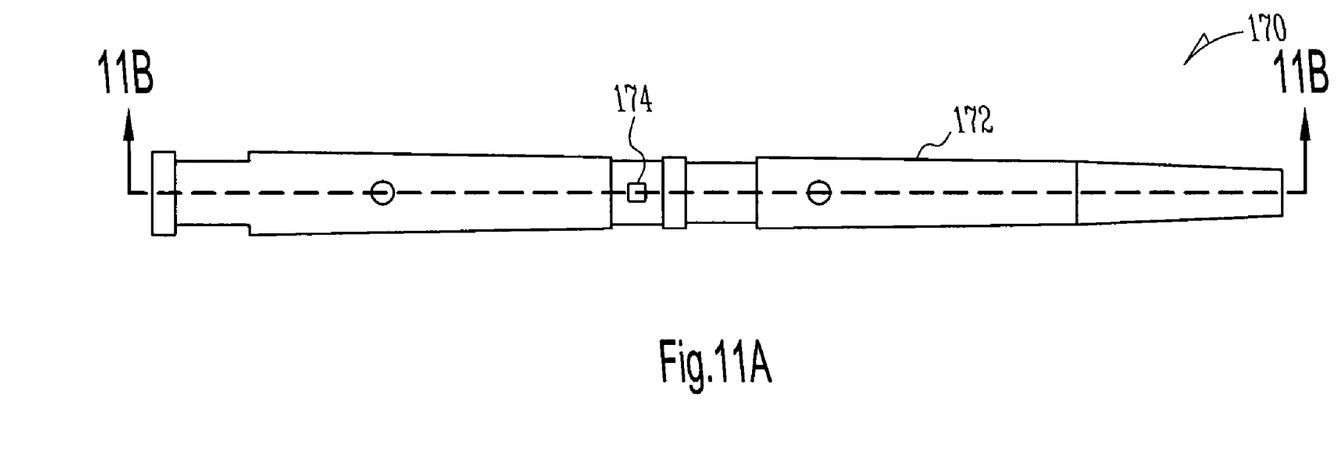
FIG. 11A is a top view of insulative material constructed in accordance with one embodiment.
Figure 11B:
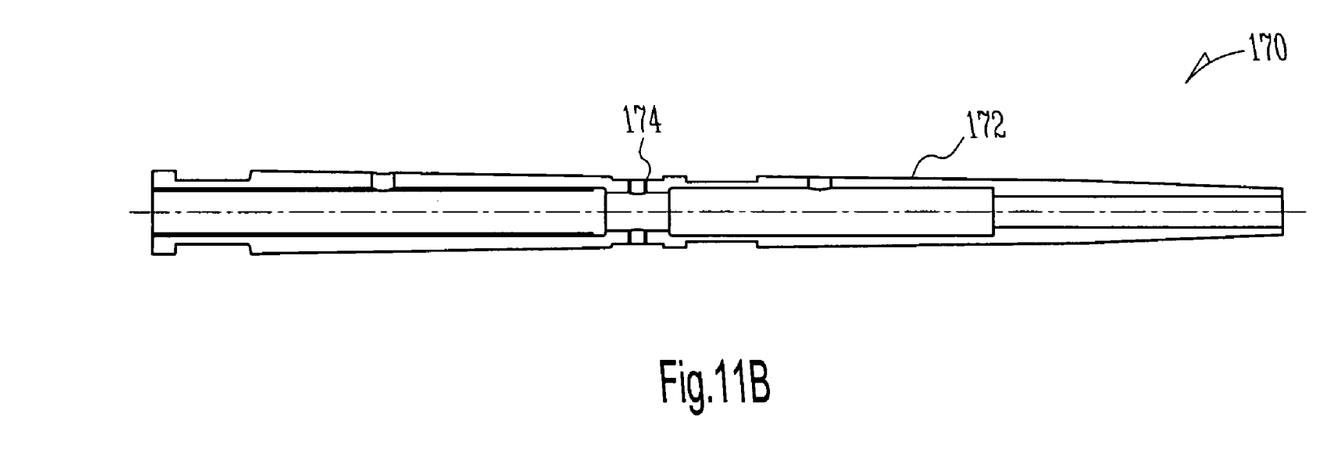
FIG. 11B is a cross-section view of insulative material constructed in accordance with one embodiment.

As mentioned above, insulative material 170 is disposed between the outer electrode 160 and the inner electrode 150 (FIG. 10). In one option, the insulative material 170 includes material that is overmolded over the inner electrode 150, formed of by a polymer, for example. In another option, the insulative material 170 includes a preformed component 172 that can be disposed over the inner electrode 150 (FIG. 3), for example, by stringing. The preformed component 172 is illustrated in greater detail in FIGS. 11A and 11B.

Figure 3:
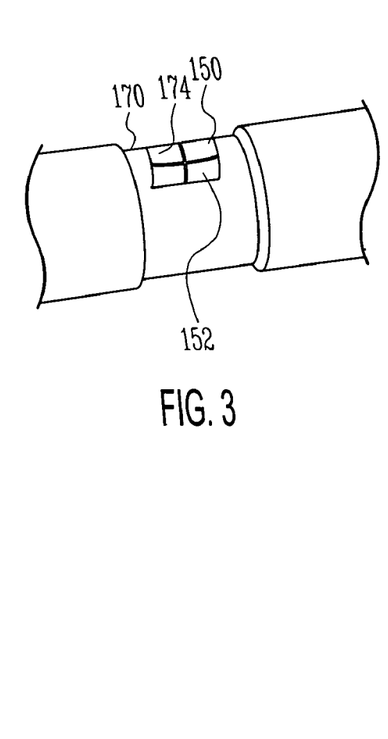
FIG. 3 is a perspective view of a portion of the lead assembly constructed in accordance with one embodiment.

The preformed component 172 is assembled over the inner electrode 150, and includes features such as a recess 174 that can mate with features of the inner electrode 150 (FIG. 3). In one option, the recess 174 has substantially the same cross-sectional shape as the one or more projections of the inner electrode 150, and the one or more projections are disposed within the recess 174, as illustrated in FIG. 3. For example, in one option, the recess 174 has a square shape, and is adapted to be strung over with an inner electrode 150 with a coupling projection that has an outer square shape. In yet another option, the recess 174 is sized smaller than the outer dimension of the one or more projections, allowing for the insulative material 170 to further seal against the one or more projections. In one option, the insulative material extends along the length of the inner electrode, as shown in FIGS. 7 and 10.

A method is further provided where the method includes coupling a conductor with an inner electrode, and an outer electrode, for example for the components and various embodiments discussed above and/or illustrated in the drawings. The coupling of the inner electrode and the conductor allows for, in one option, alignment of the inner electrode and the conductor, i.e. visually.

The method includes coupling a conductor with an inner electrode, disposing insulative material over the conductor and inner electrode, disposing an outer electrode over the inner electrode and disposing the insulative material such that insulative material extends between an inner surface of the outer electrode and an outer surface of the inner electrode, or along a length of the inner electrode, for example with a preformed insulative component. The method further includes coupling the outer electrode with the inner electrode with an optional coupling projection of the inner electrode, for example by laser welding the outer electrode to the inner electrode.

Several options for the method are as follows. For instance, in one option the inner electrode includes a non-annular projection extending therefrom to which the outer electrode is coupled. In another option, the method further includes aligning the outer electrode with the inner electrode prior to coupling the outer electrode with the inner electrode. In yet another option, the method includes disposing one or more recesses over one or more coupling projections of the inner electrode.

Advantageously, the above-discussed and illustrated design assists in providing an internal to pass through the electrode assembly, increase the performance of the lead under axial load. The conductor is sealed from the outside environment, preventing leaks under chronic applications. Furthermore, the preformed component of insulative material can reduce loss associated with an in-line molding process.

It is to be understood that the above description is intended to be illustrative, and not restrictive. Although the use of the implantable device has been described for use as a lead in, for example, a cardiac stimulation system, the implantable device could as well be applied to other types of body stimulating systems. Furthermore, it should be noted that the embodiments, and various options described above and illustrated in the drawings, may be selectively combined to form additional embodiments. Many other embodiments will be apparent to those of skill in the art upon reviewing the above description. The scope should, therefore, be determined with reference to the appended claims, along with the full scope of equivalents to which such claims are entitled.

What is claimed is:

1. A lead assembly comprising:
   at least one conductor extending from a conductor proximal end to a conductor distal end;
   an inner electrode coupled with the at least one conductor, the inner electrode defined in part by an inner electrode inner surface, an inner electrode outer surface, a first end, and a second end;
   an outer electrode disposed over the inner electrode, the outer electrode coupled with at least a portion of the inner electrode, the inner electrode and the outer electrode having a void therebetween;
   insulative material disposed between a portion of the inner and outer electrodes within the void; and
   means for aligning the outer electrode with the inner electrode for the coupling process, including, at least in part, one or more sight marks on the inner electrode.

2. The lead assembly as recited in claim 1, wherein the inner electrode and the outer electrode are coupled together along at least one coupling projection extending between the inner electrode outer surface and an outer electrode inner surface.

3. The lead assembly as recited in claim 2, wherein the inner electrode outer surface includes the at least one coupling projection extending therefrom.

4. The lead assembly as recited in claim 3, wherein the at least one coupling projection is defined in part by a projection outer surface, the projection outer surface including the one or more sight marks thereon.

5. The lead assembly as recited in claim 1, wherein the means for aligning further includes one or more outer electrode alignment features.

6. The lead assembly as recited in claim 5, wherein the one or more outer electrode alignment features include at least one sight hole extending from an outer electrode outer surface to an outer electrode inner surface.

7. The lead assembly as recited in claim 2, wherein the at least one coupling projection has a cross-section with one or more substantially flat sides.

8. The lead assembly as recited in claim 2, wherein the inner electrode extends from a first end to a second end, and the at least one coupling projection extends substantially from the first end to the second end.

9. A lead assembly comprising:
   at least one conductor extending from a conductor proximal end to a conductor distal end;
   an inner ring electrode coupled with the at least one conductor, the inner ring electrode defined in part by an inner electrode inner surface, an inner electrode outer surface and inner electrode end surfaces;
   an outer electrode disposed over the inner ring electrode, the outer electrode coupled with at least a portion of the inner ring electrode, the inner ring electrode and the outer electrode having a void therebetween;
   insulative material disposed between a portion of the inner ring and outer electrodes within the void; and
   the inner ring electrode and the outer electrode coupled together along at least one non-annular coupling projection disposed between the inner ring electrode and the outer electrode.

10. The lead assembly as recited in claim 9, wherein the at least one non-annular coupling projection has a substantially square shaped cross-section.

11. The lead assembly as recited in claim 9, wherein the at least one non-annular coupling projection has a coupling projection length substantially as long as the inner ring electrode.

12. The lead assembly as recited in claim 9, wherein the at least one non-annular coupling projection has a projection length substantially as long as the outer electrode.

13. The lead assembly as recited in claim 9, wherein the insulating material is a preformed component.

14. The lead assembly as recited in claim 9, wherein the insulating material includes at least one recess, and the at least one non-annular coupling projection is disposed within the at least one recess.

15. The lead assembly as recited in claim 14, wherein the at least one recess is smaller than the at least one non-annular coupling projection.

16. A lead assembly comprising:
   at least one conductor extending from a conductor proximal end to a conductor distal end;
   an inner electrode defined in part by an inner electrode inner surface, an inner electrode outer surface, a first end, and a second end, the inner electrode inner surface coupled with, and substantially surrounding, the at least one conductor along a portion of an inner electrode length;
   an outer electrode disposed over the inner electrode, the outer electrode coupled with at least a portion of the inner electrode, the inner electrode and the outer electrode having a void therebetween;

insulative material disposed between a portion of the inner and outer electrodes within the void, the insulative material extending between the first end and the second end; and the inner electrode and the outer electrode coupled together along at least one coupling projection disposed between the inner electrode and the outer electrode.

17. The lead assembly as recited in claim 16, wherein the at least one coupling projection has a projection length substantially as long as the outer electrode.

18. The lead assembly as recited in claim 16, wherein insulation is a preformed component.

19. The lead assembly as recited in claim 18, wherein insulation includes at least one recess, and the at least one coupling projection is disposed within the at least one recess.

20. The lead assembly as recited in claim 19, wherein the at least one recess is smaller than the at least one coupling projection.

21. The lead assembly as recited in claim 16, wherein the at least one coupling projection is defined in part by a projection outer surface, the projection outer surface including alignment features thereon.

22. The lead assembly as recited in claim 21, wherein the outer electrode includes one or more outer electrode alignment features therein.

23. The lead assembly as recited in claim 16, wherein the inner electrode includes the at least one coupling projection extending therefrom.

24. A lead assembly comprising:
at least one conductor extending from a conductor proximal end to a conductor distal end;
an inner electrode coupled with the at least one conductor, the inner electrode defined in part by an inner electrode inner surface, an inner electrode outer surface and inner electrode end surfaces;
an outer electrode disposed over the inner electrode, the outer electrode coupled with at least a portion of the inner electrode along at least one annular coupling projection, the inner electrode and the outer electrode having a void therebetween; and
insulative material disposed between a portion of the inner and outer electrodes within the void, the insulative material extending between an outer electrode inner surface to at least a portion of the inner electrode outer surface.

25. The method as recited in claim 24, wherein the inner electrode is formed using at least one of injection molding or electrical discharge machining.

26. The lead assembly as recited in claim 24, wherein an outer surface of the at least one annular coupling projection includes a slightly rounded outer profile.

27. The lead assembly as recited in claim 24, wherein the at least one annular coupling projection extends from a portion of the inner electrode outer surface.

28. The lead assembly as recited in claim 24, wherein the insulative material includes a preformed component.

29. The lead assembly as recited in claim 24, wherein the insulative material includes a polymer overmolded on the inner electrode.

30. A lead assembly comprising:
at least one conductor extending from a conductor proximal end to a conductor distal end;
an inner electrode coupled with the at least one conductor, the inner electrode defined in part by an inner electrode inner surface, an inner electrode outer surface, a first end, and a second end;
an outer electrode disposed over the inner electrode, the outer electrode coupled with at least a portion of the inner electrode, the inner electrode and the outer electrode having a void therebetween;
insulative material disposed between a portion of the inner and outer electrodes within the void; and
means for aligning the outer electrode with the inner electrode for the coupling process, including, at least in part, one or more sight marks formed on a coupling projection of the inner electrode.

31. The lead assembly as recited in claim 30, wherein the insulative material comprises silicone tubing.

32. The lead assembly as recited in claim 30, wherein the one or more sight marks include one or more cross-hairs formed, printed, or etched on a portion of the inner electrode.

33. The lead assembly as recited in claim 30, wherein the means for aligning further includes one or more outer electrode alignment features.

34. The lead assembly as recited in claim 33, wherein the one or more outer electrode aligment features includes a sight hole.

35. The lead assembly as recited in claim 30, wherein the insulating material includes a preformed component, the preformed component having at least one recess smaller in size than the coupling projection of the inner electrode.

36. The lead assembly as recited in claim 30, wherein the insulative material includes a polymer overmolded on the inner electrode.

* * * * *

UNITED STATES PATENT AND TRADEMARK OFFICE
CERTIFICATE OF CORRECTION

| | | |
|---|---|---|
| PATENT NO. | : 7,212,868 B2 | Page 1 of 1 |
| APPLICATION NO. | : 10/813496 | |
| DATED | : May 1, 2007 | |
| INVENTOR(S) | : McAuliffe et al. | |

It is certified that error appears in the above-identified patent and that said Letters Patent is hereby corrected as shown below:

In column 8, line 40, in Claim 34, delete "aligment" and insert -- alignment --, therefor.

Signed and Sealed this

Third Day of July, 2007

JON W. DUDAS
*Director of the United States Patent and Trademark Office*